United States Patent [19]

Walsh

[11] Patent Number: 4,619,248

[45] Date of Patent: Oct. 28, 1986

[54] LIGHT ATTACHMENT FOR SPECULUM

[76] Inventor: David J. Walsh, 2512 Mississauga Road, Mississauga, Ontario, Canada, L5H 2L5

[21] Appl. No.: 767,208

[22] Filed: Aug. 19, 1985

[30] Foreign Application Priority Data

Aug. 22, 1984 [CA] Canada .................................. 461581

[51] Int. Cl.⁴ ........................... A61B 1/06; A61B 1/30
[52] U.S. Cl. ...................................... 128/18; 362/109; 362/804
[58] Field of Search ....................... 128/18, 17, 16, 22, 128/23; 362/109, 804

[56] References Cited

U.S. PATENT DOCUMENTS 3,246,646  4/1966  Murphy, Jr. ........................... 128/17
3,789,835  2/1974  Whitman ................................ 128/18
4,067,323  1/1978  Troutner et al. ...................... 128/18

Primary Examiner—William H. Grieb
Attorney, Agent, or Firm—Hirons, Rogers & Scott

[57] ABSTRACT

This invention provides a lighting source for use with a speculum. The source includes a casing having a hoop and a main portion, and a light emitter coupled to the hoop at a location diametrically opposite the main portion. An electrical energy source is contained in the main portion and the energy source is coupled to the light emitter. Switch means is provided for selectively operating the light emitter and the structure is attachable to a speculum with the light emitter positioned to illuminate the body opening when viewed through the hoop.

5 Claims, 4 Drawing Figures

LIGHT ATTACHMENT FOR SPECULUM

This invention relates to a lighting attachment for use with specula and more particularly for use with a vaginal speculum.

In order to illustrate a preferred embodiment, the invention will be described in use with a vaginal speculum of a type having two deflectors which can be adjusted both by movement apart and by angular movement relative to one another. Such a speculum is described in U.S. Pat. No. 3,246,646 to Murphy. However, it will be appreciated that the invention is adaptable for use with other specula of different types and for other purposes.

The exemplary prior art speculum consists of first and second parts loosely connected to one another for relative angular and linear movement. The parts include respective deflectors and handle portions arranged so that with the handle portions angled to one another the deflectors are generally parallel and linear movement will cause the deflectors to separate while remaining in this relationship. The handle portions can be moved angularly towards one another so that the deflectors move apart to dilate the body opening being examined.

In use one of the handle portions is outermost and this defines an opening for viewing between the deflectors. Also, this portion defines a pair of fingers which engage in a slot in the other handle portion and include detents to retain the angular position of one handle portion relative to the other by engagement with the sides of the slot. The slot of course is necessary to permit the linear motion previously described.

These fingers between them define an outwardly opening recess and use is made of this recess to engage the lighting attachment of the present invention and to automatically actuate the attachment for illuminating the dilated body opening.

Previous lighting attachments used with vaginal specula have included a structure which resembles a flashlight having a fibre-optic light tube at its end. The main body of the lighting attachment is attached to an outer handle portion of the speculum and the light tube curves from this portion into an opening for illumination during examination. In order that the device does not occlude the opening, the light tube necessarily terminates at a portion of the opening in the first part adjacent the body of the lighting attachment or in other words at the bottom of the opening. It therefore will direct light satisfactorily only when the speculum is in its maximum open position because otherwise a portion of the first part will be in line with the light source and prevent direct lighting during examination. An attempt to provide lighting in the right position was made by clipping a fibre-optic light source to the top of the opening in the first part so that it would then move with this part and always shine just under the deflector associated with this part. This would avoid the problem of occlusion but causes another problem in that it required a clip which was not very secure and the lighting was done with a fibre-optic light tube so that during use there was a tendency for the light tube to be a nuisance.

The present invention is intended to overcome the problems of the prior art and to provide a simple light source which is self-contained and which will attach readily to a speculum, particularly of the Murphy type, and which is inexpensive and disposable after the electrical energy source contained in the device has become de-energized.

Accordingly in one of its aspects the invention provides a lighting source for use with a speculum. The source includes a casing having a hoop and a main portion, and a light emitter coupled to the hoop at a location diametrically opposite the main portion. An electrical energy source is contained in the main portion and the energy source is coupled to the light emitter. Switch means is provided for selectively operating the light emitter and the structure is attachable to a speculum with the light emitter positioned to illuminate the body opening when viewed through the hoop.

The invention will be better understood with reference to the following description taken in combination with the drawings, in which:

FIG. 1 is a perspective view of an exemplary speculum according to U.S. Pat. No. 3,246,646 shown with a preferred embodiment of a lighting attachment according to the invention to demonstrate how the attachment would fit into and be used with the speculum;

Figure 1:
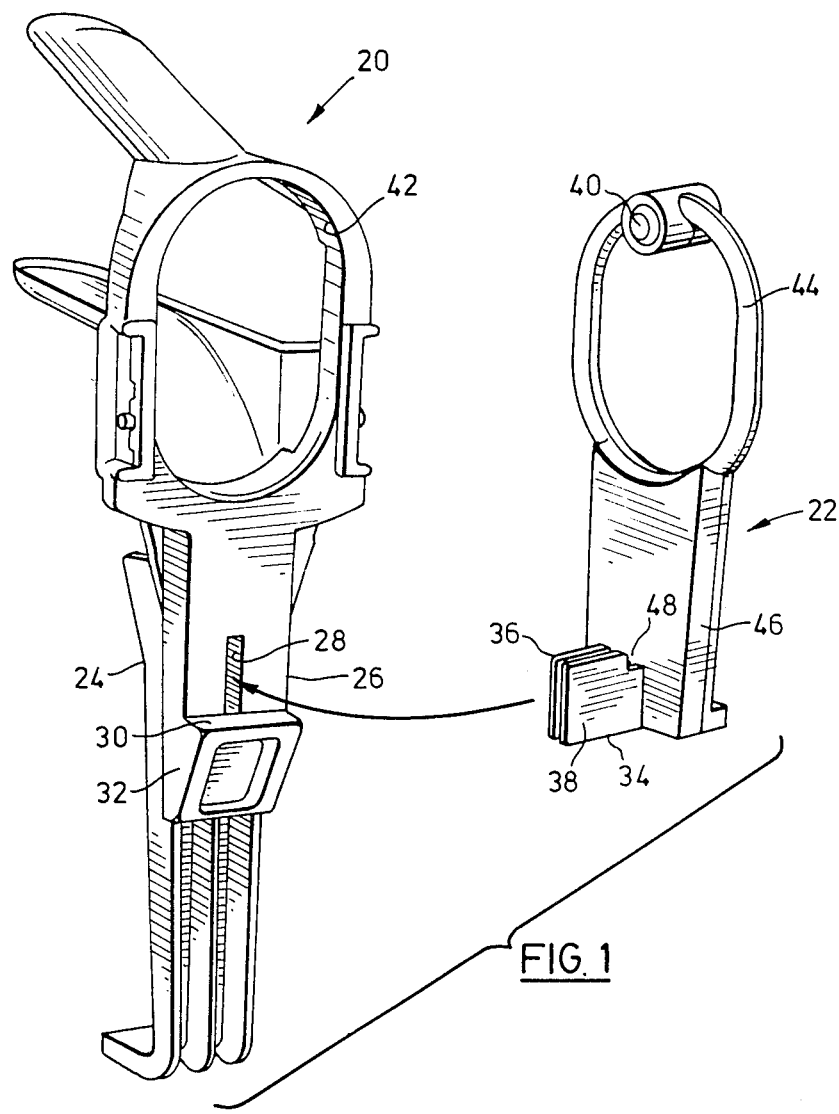

Reference is made firstly to FIG. 1 which shows the exemplary Murphy speculum designated generally by the numeral 20 and a preferred embodiment of the lighting attachment according to the present invention and designated generally by the numeral 22.

The speculum 20 includes first and second parts 24, 26 which are moveable relative to one another both by sliding and by pivoting. The second or outer part 26 defines a recess 28 adjacent a step 30 at the upper extremity of a thumb-engagement portion 32. Lighting attachment 22 is coupled to the speculum by engaging a coupling 34 in the recess 28. The coupling consists of first and second plates 36, 38 which when brought into contact with one another close the circuit to energize a bulb 40. As will be described, the recess 28 is tapered so that when the plates are pushed into the recess they are deflected into contact with one another to close the circuit.

To engage the lighting attachment 22, it is tilted so that the bulb 40 is nearer to the speculum and the coupling 34 is engaged in the recess 28. As the movement continues, the attachment takes a position generally parallel to a portion of the speculum around an opening 42 in the first part 26 of the speculum. The bulb 40 is then in position to illuminate through the opening 42 and observation is made through a hoop 44 carrying the bulb 40 and attached to a main portion 46 of the attachment.

It will be seen that the plates 36, 38 of the coupling 34 define a notch 48 so that when the attachment is in place, any tendency in use to rotate the attachment so that the bulb moves away from the speculum will be resisted by the notch coming into engagement with a wall of the outer part adjacent the recess 28 to retain the attachment in place. It can of course be removed by reversing the tilting action used to engage it.

Details of the structure of the attachment 22 will now be described with reference to FIG. 2 and subsequently the use of the attachment with the exemplary speculum 20 will be described with reference to FIGS. 3 and 4.

Figure 2:
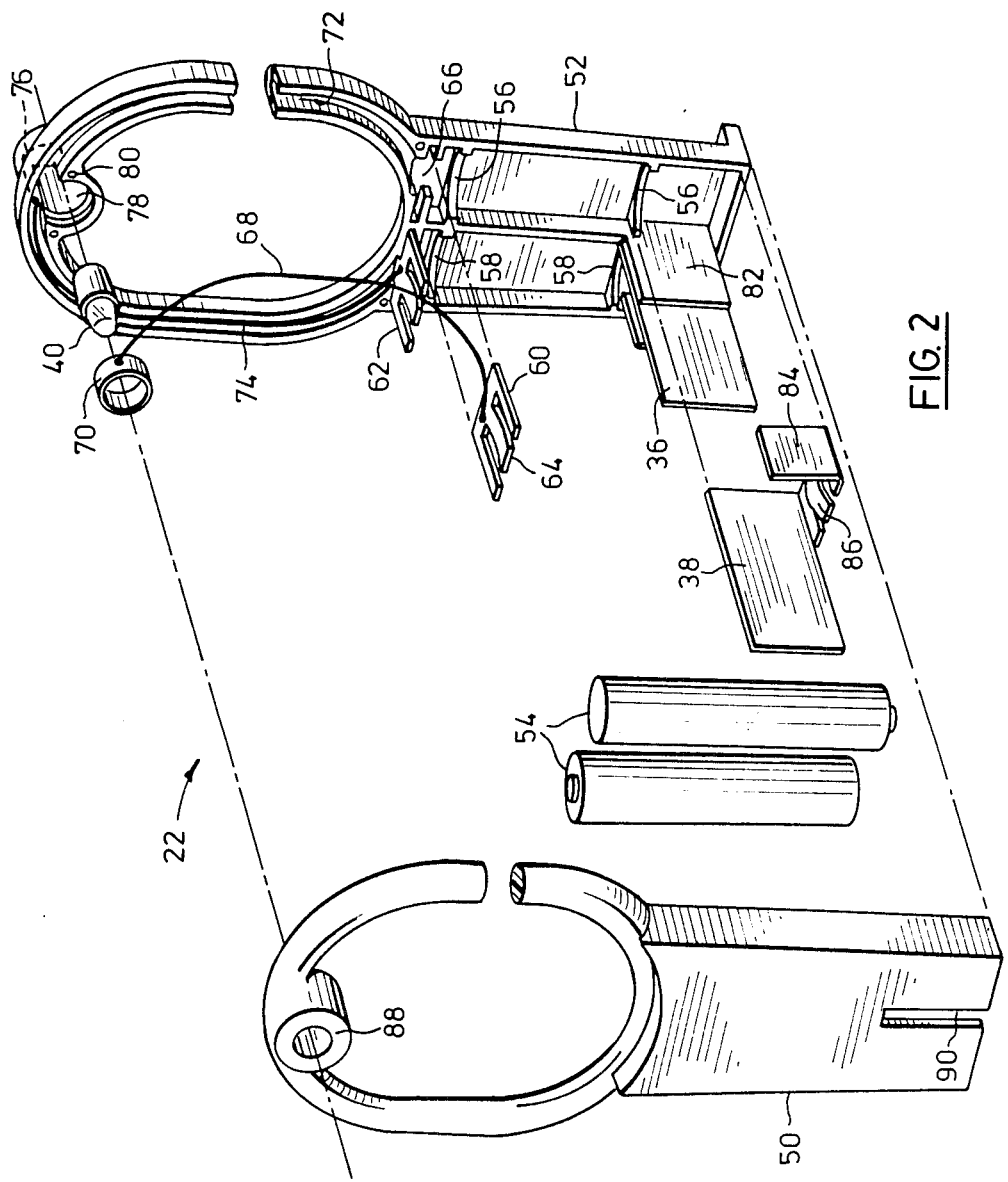
FIG. 2 is an exploded perspective view with the portions broken away to show the lighting attachment.

As seen in FIG. 2, the attachment 22 includes first and second moulded elements 50, 52 which together form a casing. A main portion of the casing contains a pair of electrical storage cells 54 which are used to energize the bulb 40. Casing element 52 defines pairs of saddles 56 and 58 which locate and support the respective cells 54. Adjacent upper saddles 56, 58 (as drawn) are a pair of contacts 60, 62 which make engagement with the upper ends of the respective cells 54. It will be noted that these cells are arranged so that the positive pole of one cell makes engagement with contact 62 whereas the negative pole of the other cell engages contact 60. As seen with reference to contact 60, a central tongue 64 is deformed to provide slight spring bias for better contact with the cell.

Contact 60 engages in a slot 66 formed in the element 52 and contact 62 engages in a corresponding slot. A conductor 68 connects contact 62 to a contact ring 70 and the conductor is contained in a groove 72 formed in part of the hoop 44 (FIG. 1) formed by element 52. Correspondingly, a conductor 74 connects the contact 62 to an end piece 76 in a housing 78 which contains the bulb 40 and associated ring 70. Consequently with the bulb in position, the bulb contact is connected to the end piece 76.

The element 50 has locating pins moulded into the structure (not shown) for engagement in corresponding openings such as opening 80 in the element 52 so that when the two elements are brought together they will locate and can be either adhered or welded to one another.

Element 52 includes an integrally moulded tongue 82 between the batteries and separating the conductive blades 36, 38. The blade 38 is typical of both blades and it will be seen in FIG. 2 that integral with the blade is a battery connector consisting of a locating upstanding part 84 and between the blade 38 and the part 84 is a deformed tongue 86 providing bias for better engagement with the cell. The blade 38 and associated parts fits between saddle 56 and the bottom of the casing and is held in place by its proportions in this relationship.

When the two elements 50, 52 of the casing are brought together, the element 50 includes an end wall 88 having a central opening for locating and holding the bulb in the housing 78. This end wall is formed integrally with the portion of the hoop defined by element 50 and this hoop portion simply covers the groove 72 and of course adds some rigidity to the structure.

The blades 36, 38 together with part of the tongue 82 project through a slot 90 formed in the element 50. Because the blades 36, 38 are connected electrically to the cells 54, by bringing the blades together, the cells are brought into series with one another and the circuit completed to energize the bulb 40. This simple expedient of providing contacts for the cells and in effect a switch between the cells makes for a particularly simple structure.

Figures 3, 4:
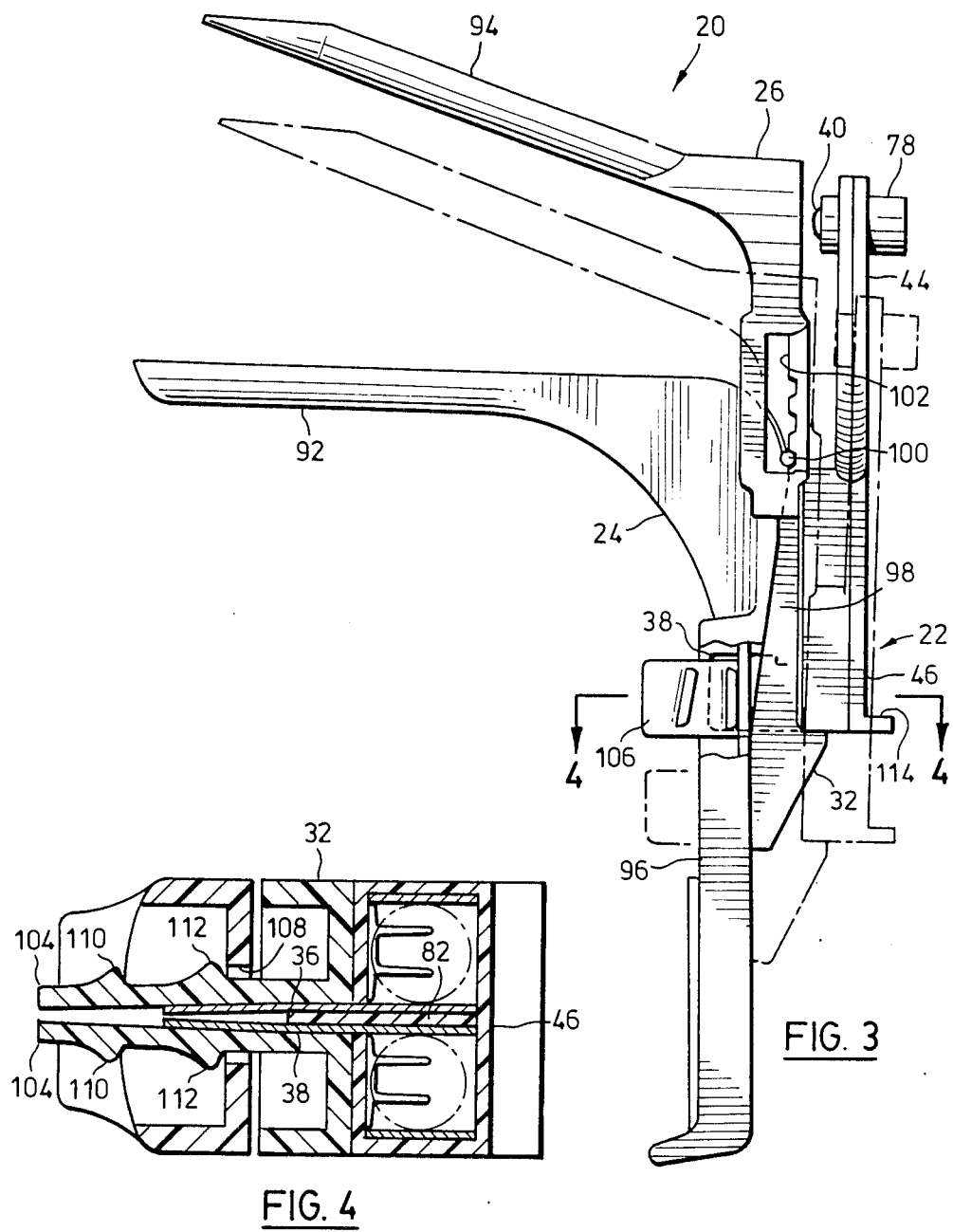
FIG. 3 is a side view with portions broken away and illustrating the speculum with the lighting attachment in position to be used with the speculum.
FIG. 4 is a sectional top view on line 4—4 of FIG. 3.

Reference is now made to FIG. 3 which shows the speculum in position to dilate a body cavity and, in ghost outline, an intermediate position. Initially, the respective deflectors 92, 94 of the first and second parts 24, 26 lie in generally parallel arrangement and close together. This position (which is not shown in the drawings) would result in respective hand portions 96, 98 being separated angularly from one another pivoting about the pair of pivot pins, 100 (one of which is shown). At this point the pins would be at upper ends (as drawn) of respective slots 102. Also, a pair of fingers 104, 106 (see also FIG. 3) forming projections of the outer part 26 would be disengaged from the inner part 24.

The user has two alternatives to cause dilation. Firstly the hand parts can be brought together into the ghost-outline position and then by sliding the outer part upwardly (as drawn) the pivots 100 would move in the slot and the fingers 104, 106 would engage in a slot 108 formed in the first part 24. This slot is enlarged below the section line so that in the initial angular movement the fingers move freely without engagement but as soon as the second part is moved upwardly, they engage behind the slot and pairs of detents 110, 112 (best seen in FIG. 4) come into play.

Alternatively, the outer part can be moved from the initial position where the deflectors are adjacent one another by moving the pivot along the slot while maintaining the deflectors in a parallel arrangement. The handle portions are then moved angularly about the first pins 100 and into the FIG. 3 position thereby causing the fingers 104, 106 to snap through the slot as they are deflected by engagement by the detents 110, 112. Obviously, either pair of detents can be used depending on the angular movement needed for dilation.

With this background, it will be evident that when the lighting attachment is engaged into the recess 28 (FIG. 1) the plates 36, 38 together with part of the tongue 82 engage between the fingers 104, 106. Because these fingers are tapered towards one another, the plates 36, 38 are deflected into the FIG. 4 position where the ends are in contact to complete the circuit and illuminate the bulb 40.

In use, the lighting attachment can be coupled to the speculum at any time either before insertion or afterwards. It will not interfere with the operation of the speculum because the thumb engagement portion 32 (FIG. 3) is still available for pushing the outer part upwards relative to the inner part of the speculum and when it is desired to reverse this movement, a lip 114 on the outward facing part of the attachment (FIG. 3) can be gripped by the thumb to pull the part 26 downwardly.

It will be evident from the foregoing description that the lighting attachment can take various forms within the scope of the invention consistent with providing a convenient and inexpensive device providing a light emitter where it gives maximum illumination without occluding the viewing opening for seeing between the deflectors. Such forms are within the scope of the invention.

I claim:

1. A lighting attachment for use with a speculum of the type comprising first and second parts movable relative to one another to dilate a body opening for examination, the first part having a first handle portion defining a slot and a first deflector extending generally perpendicularly from the first handle portion, the second part having a pair of parallel fingers including locating detents, the fingers being engaged in the slot and defining between them an outwardly opening recess, the second part also having a second deflector extending generally parallel to the first deflector with the fingers out of the slot and movable angularly away from the first deflector causing the fingers to move into the body opening, the fingers then being deflected slightly towards one another to bias the detents to hold the fingers in the slot, the lighting attachment comprising:

an elongate casing having a main portion and a hoop lying generally in the same plane as the main portion;
an electrical energy source contained in the main portion;
a light emitter attached to the hoop at a location diametrically opposite the main portion;
circuit means coupling the light emitter to the electrical energy source and including switch means for energizing the light emitter; and
the switch means comprising a pair of conductors normally spaced from one another and proportioned for engagement in the recess so that with the fingers deflected, the conductors are flexed towards and into engagement with one another to thereby switch on the light emitter and project light between the deflectors to illuminate the body opening for examination by viewing through the hoop.

2. A lighting attachment as claimed in claim 1 in which the energy source is a pair of electrical storage cells.

3. A lighting attachment as claimed in claim 1 in which the casing includes an insulating projection between portions of the conductors adjacent the casing.

4. A lighting source for use with a speculum for use in dilating body openings to make medical examinations, the source comprising:
a casing including a hoop and a main portion;
a light emitter coupled to the hoop at a location diametrically opposite the main portion;
an electrical energy source contained in the main portion;
means coupling the energy source to the light emitter and including switch means for selectively operating the light emitter;
means operable to attach the source to a speculum with the light emitter positioned to illuminate the body opening when viewed through the hoop.

5. A lighting attachment as claimed in claim 1 in which the main portion includes an outwardly-facing step for use in causing relative movement between the parts with the attachment coupled to the second part.

* * * * *